(12) United States Patent
Patience et al.

(10) Patent No.: US 9,145,350 B2
(45) Date of Patent: Sep. 29, 2015

(54) METHODS FOR THE VALORIZATION OF CARBOHYDRATES

(75) Inventors: Gregory Patience, Town of Mount Royal (CA); Ali Shekari, Montréal (CA); Youssef Farrie, Montreal (CA)

(73) Assignee: POLYVALOR, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 14/241,389

(22) PCT Filed: Aug. 22, 2012

(86) PCT No.: PCT/CA2012/000781
§ 371 (c)(1),
(2), (4) Date: Jun. 17, 2014

(87) PCT Pub. No.: WO2013/029149
PCT Pub. Date: Mar. 7, 2013

(65) Prior Publication Data
US 2014/0309454 A1    Oct. 16, 2014

Related U.S. Application Data

(60) Provisional application No. 61/527,711, filed on Aug. 26, 2011.

(51) Int. Cl.
| | |
|---|---|
| *C07C 51/21* | (2006.01) |
| *C07C 51/31* | (2006.01) |
| *B01J 25/00* | (2006.01) |
| *B01J 23/889* | (2006.01) |
| *B01J 21/06* | (2006.01) |
| *B01J 23/00* | (2006.01) |
| *B01J 23/42* | (2006.01) |
| *B01J 23/44* | (2006.01) |
| *B01J 23/46* | (2006.01) |
| *B01J 23/52* | (2006.01) |
| *B01J 23/54* | (2006.01) |
| *B01J 23/63* | (2006.01) |
| *B01J 23/72* | (2006.01) |
| *B01J 23/745* | (2006.01) |
| *B01J 23/755* | (2006.01) |
| *B01J 23/80* | (2006.01) |
| *B01J 23/83* | (2006.01) |
| *B01J 23/89* | (2006.01) |
| *B01J 27/185* | (2006.01) |
| *B01J 27/198* | (2006.01) |
| *B01J 29/12* | (2006.01) |
| *B01J 29/44* | (2006.01) |
| *B01J 29/46* | (2006.01) |
| *B01J 29/48* | (2006.01) |
| *B01J 25/02* | (2006.01) |

(52) U.S. Cl.
CPC ............. *C07C 51/313* (2013.01); *B01J 21/066* (2013.01); *B01J 23/002* (2013.01); *B01J 23/42* (2013.01); *B01J 23/44* (2013.01); *B01J 23/462* (2013.01); *B01J 23/464* (2013.01); *B01J 23/52* (2013.01); *B01J 23/54* (2013.01); *B01J 23/63* (2013.01); *B01J 23/72* (2013.01); *B01J 23/745* (2013.01); *B01J 23/755* (2013.01); *B01J 23/80* (2013.01); *B01J 23/83* (2013.01); *B01J 23/8892* (2013.01); *B01J 23/8986* (2013.01); *B01J 25/00* (2013.01); *B01J 27/1853* (2013.01); *B01J 27/198* (2013.01); *B01J 29/126* (2013.01); *B01J 29/44* (2013.01); *B01J 29/46* (2013.01); *B01J 29/48* (2013.01); *C07C 51/21* (2013.01); *B01J 25/02* (2013.01)

(58) Field of Classification Search
CPC ...... C07C 51/21; C07C 51/313; B01J 23/002; B01J 23/43; B01J 23/44; B01J 23/52; B01J 23/54; B01J 23/63; B01J 23/80; B01J 23/83; B01J 23/462; B01J 23/464; B01J 23/745; B01J 23/8892; B01J 23/8986; B01J 21/066; B01J 25/00; B01J 25/02; B01J 27/198; B01J 27/1853; B01J 29/44; B01J 29/46; B01J 29/48; B01J 29/126
USPC ......................................................... 562/515
See application file for complete search history.

(56) References Cited

U.S. PATENT DOCUMENTS

| | | | |
|---|---|---|---|
| 3,888,886 A | 6/1975 | Young et al. | |
| 5,109,128 A * | 4/1992 | Schumacher et al. | ........ 536/124 |
| 5,132,452 A | 7/1992 | Deller et al. | |
| 5,132,542 A * | 7/1992 | Bassalleck et al. | ...... 250/370.09 |
| 5,821,360 A * | 10/1998 | Engelskirchen et al. | ..... 536/124 |
| 5,847,163 A * | 12/1998 | Mazzoni et al. | .............. 549/259 |
| 7,671,246 B2 | 3/2010 | Dumesic et al. | |

(Continued)

FOREIGN PATENT DOCUMENTS

| | | |
|---|---|---|
| CA | 2193910 | 6/1997 |
| CA | 2730260 | 1/2010 |

(Continued)

OTHER PUBLICATIONS

Thompson, David T., "An overview of gold-catalysed oxidation processes", Topics in Catalysis, vol. 38, No. 4, Aug. 2006, pp. 231-240.
Odebunmi et al., "Homogenous catalytic oxidation of some sugars: A review", Current Research in Chemistry, vol. 3, No. 1, pp. 16-28, 2011.

(Continued)

*Primary Examiner* — Shailendra Kumar
(74) *Attorney, Agent, or Firm* — Bereskin & Parr LLP/S.E.N.C.R.L., s.r.l.

(57) ABSTRACT

There are provided methods for the valorization of carbohydrates. The methods comprise reacting a fluid comprising at least one carbohydrate with at least one metal catalyst or at least one metal catalytic system in a fluidized bed reactor so as to obtain at least one organic acid or a derivative thereof.

15 Claims, 2 Drawing Sheets

(56) References Cited

U.S. PATENT DOCUMENTS

| | | |
|---|---|---|
| 8,277,643 B2 | 10/2012 | Huber et al. |
| 2003/0109746 A1 | 6/2003 | Fiorentino et al. |
| 2011/0124889 A1* | 5/2011 | Saladino et al. ............ 549/477 |

FOREIGN PATENT DOCUMENTS

| | | |
|---|---|---|
| EP | 0804963 | 11/1997 |
| EP | 1202017 | 5/2002 |
| WO | 2011031320 | 3/2011 |

OTHER PUBLICATIONS

Tandioy, O. M., "Modeling of maleic anhydride production from a mixture of n-butane and butenes in fluidized bed reactor", Latin American Applied Research, vol. 39, pp. 19-26, 2009.

Published by SpringerLink, "Waste and Biomass Valorization", Journal No. 12649, 2010, Retrieved from the Internet <http://www.springer.com/engineering/journal/12649>.

Merriam-Webster Dictionary, 2015 Encyclopaedia Britannica Company, Retrieved from the Internet <http://www.merriam-webster.com/dictionary/valorize>.

* cited by examiner

METHODS FOR THE VALORIZATION OF CARBOHYDRATES

CROSS-REFERENCE TO RELATED APPLICATIONS

The present application is a 35 USC 371 national stage entry of PCT/CA2011/000781 filed on Aug. 22, 2012, that claims priority on U.S. 61/527,711 filed on Aug. 26, 2011. These documents are hereby incorporated by reference in their entirety.

TECHNICAL FIELD

The present disclosure relates to improvements in the field of chemistry and chemical engineering applied to the preparation of organic compounds. More particularly, it relates to methods for the valorization of carbohydrates.

BACKGROUND OF THE DISCLOSURE

There are many paths to adding value to carbohydrates from the simple thermal treatments—combustion, gasification, pyrolysis, and liquefaction—to enzymatic processes. In the former, energy is the goal or simple molecules like hydrogen and CO that can be used to as a feedstock leading to methanol, olefins, methane, diesel, etc. In the latter, the principal target molecules are alcohols—ethanol, butanol—for fuel. The major cost factors of the sugar-to-alcohol process include feedstock, enzyme, and fermentation. Fermentation is an inherently inefficient process in which maximum carbon yields of better than 50% are difficult to achieve.

There is thus a need for providing alternative methods for the valorization of carbohydrates. Moreover, there is a need for providing methods that would overcome at least one of the drawbacks of the methods found in the prior art.

SUMMARY OF THE DISCLOSURE

According to one aspect, there is provided a method for the valorization of carbohydrates, the method comprising:
  reacting a fluid comprising at least one carbohydrate with at least one metal catalyst or at least one metal catalytic system in a fluidized bed reactor so as to obtain at least one organic acid or a derivative thereof.

According to another aspect, there is provided a method for the valorization of carbohydrates, the method comprises:
  reacting a fluid comprising at least one carbohydrate with at least one metal catalyst or at least one metal catalytic system under conditions suitable for at least substantially preventing caramelization of the at least one carbohydrate, so as to obtain at least one organic acid or a derivative thereof.

It was found that the methods described in the present disclosure allow for high throughput rates and high reaction rates. These methods are also efficient for being carried out in smaller reaction vessels and provide high selectivities.

It was also found that the methods of the present disclosure allow for lowering yield losses (for example versus fermentation, which is not much better than 50%) and for lowering the number of unit operations as well as the number of steps required in the production process, thereby lowering the production costs.

It was also found that by carrying out the reaction between the at least one carbohydrate and the at least one metal catalyst in fluidized bed reactor, it was possible to avoid caramelization of the at least one carbohydrate. In fact, it was observed that it was possible to avoid caramelization problems, problems that render very difficult such chemical processes for various reasons including difficult intermediates and by-products to work with (caramelized products) and degradation of the carbohydrates. Without being bound or limited to such a theory, Applicants believe that by using a fluidized bed reactor, since the heat transfer is so rapid, the at least one carbohydrate will heat up and react catalytically faster than the caramelization reaction.

It was thus observed that using a fluid bed reactor was efficient for providing conditions suitable for at least substantially preventing caramelization of the at least one carbohydrate.

It was also found that by providing reaction conditions at which the caramelization of the at least one carbohydrate is slower than the reaction between the at least one carbohydrate and the at least one metal catalyst that produces the at least one organic acid or a derivative thereof, it was possible to at least substantially prevent caramelization of the at least one carbohydrate.

It was also found that by carrying out the methods at a temperature below a temperature at which caramelization of the at least one carbohydrate is faster than the reaction between the at least one carbohydrate and the at least one metal catalyst that produces the at least one organic acid or a derivative thereof, it was possible to at least substantially prevent caramelization of the at least one carbohydrate.

Finally, it was also found that the methods of the present disclosure are effective for reacting sugars (for example pentoses) directly, that is, based on the knowledge of the applicants, currently uncommon for fermentation processes. The person skilled in the art would clearly understand that such methods could be applied to various other carbohydrates for example, to various other carbohydrates as described in the present disclosure.

BRIEF DESCRIPTION OF THE DRAWINGS

Further features and advantages of the disclosure will become more readily apparent from the following description of various embodiments as illustrated by way of examples in the appended figures wherein.

DETAILED DESCRIPTION OF VARIOUS EMBODIMENTS

Figure 1:
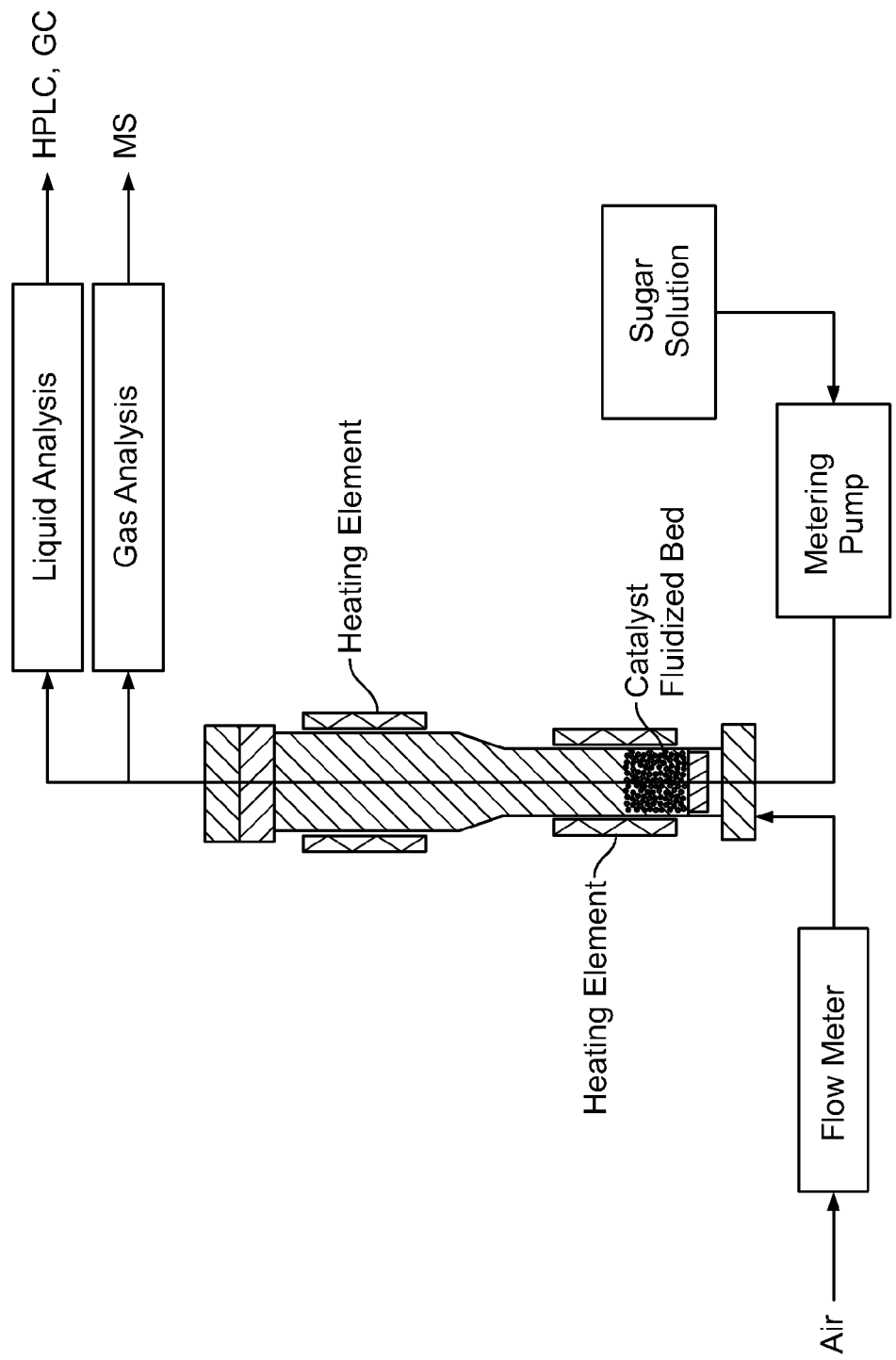
FIG. 1 is a schematic representation of an example of a reactor that can be used for carrying out the methods described in the present disclosure.

Further features and advantages will become more readily apparent from the following description of various embodiments as illustrated by way of examples only and in a non-limitative manner.

The expression "organic acid or a derivative thereof" as used herein refers to an organic acid or a derivative thereof. For example, the derivative of the organic acid can be an anhydride, a salt, an amide, an ester, an acid halide etc.

The term "suitable" as used herein means that the selection of the particular compound and/or conditions would depend on the specific manipulation to be performed, but the selection would be well within the skill of a person trained in the art. All process/method described herein are to be conducted under conditions sufficient to provide the desired product (for example at least one organic acid or a derivative thereof). A person skilled in the art would understand that all reaction conditions, including, for example, reaction time, reaction temperature, reaction pressure, reactants concentration and/or ratio, injection rates (carbohydrate or a composition thereof and/or fluidization gas) and whether or not the reaction should be performed under inert atmosphere, can be varied to optimize the yield of the desired product and it is within their skill to do so.

Terms of degree such as "about" and "approximately" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

For example, the method can comprise injecting atomized droplets of a carbohydrate-containing composition that comprises the at least one carbohydrate and water into the fluidized bed reactor.

For example, the atomized droplets can be vaporized in situ when inserted into the fluidized bed reactor.

For example, the fluid can be a gas, a liquid or a mixture thereof. According to one embodiment, the fluid can be synthetic air. According to another embodiment, the fluid can be air having a concentration of $O_2$ of about 0 to about 21%.

The carbohydrate can be at a concentration of about 1 wt % to about 20 wt %, about 2 wt % to about 18 wt %, about 5 wt % to about 15 wt %, about 10 wt % to about 15 wt %, about 8 wt % to about 12 wt %, or about 10 wt %, based on the total weight of the carbohydrate-containing composition.

For example, the composition can be injected at a rate of about 0.5 mL/minute to about 10 mL/minute, about 1 mL/minute to about 8 mL/minute, about 2 mL/minute to about 6 mL/minute or about 3 mL/minute to about 5 mL/minute per about 0.2 L of capacity of the fluidized bed reactor.

For example, the fluidization gas can be injected at a flow rate of about 100 mL to about 20000 mL/minute, 400 mL/minute to about 2000 mL/minute, about 500 mL/minute to about 1500 mL/minute, about 600 mL/minute to about 1200 mL/minute, or about 800 mL/minute to about 1000 mL/minute per 0.2 L of capacity of the fluidized bed reactor.

For example, the at least one metal catalyst or the at least one metal catalytic system can be an oxidation catalyst.

Examples of oxidation catalysts can comprise vanadium pyrophosphate, iron phosphate, VPO catalyst, $V_2O_5$ or mixtures thereof.

Examples of oxidation catalysts can comprise $VOPO_4$ (for example $\alpha$-$VOPO_4$ or $\gamma$-$VOPO_4$) $VOHPO_4$, $(VO)_2P_2O_7$, $VO(PO_3)_2$, $VO(H_2PO_4)_2$ or mixtures thereof.

Examples of oxidation catalysts can be chosen from vanadium phosphorus oxide catalysts.

Other examples of metal catalysts or metal catalytic systems can include any or a combination of Au, Pt, Rh, Ru, Pd, Cu, Ni or Fe or generally the transition metals supported over alumina, silica or zeolites as well as Mo, Re, Fe, Pd, Cu or Pt supported over HZSM-5 or Rh supported over NaY zeolites. Specific examples include supported or bulk Sn based catalysts such as $SnCl_2$ or $Cu/SiO_2$, $Cu/Al_2O_3$, $Cu/CeO_2$, $CuMnO_2$, $Cu/CuO$, $Cu/CuO/Al_2O_3$, $Cu/ZnO/Al_2O_3$, $Cu/ZnO/Cr_2O_3$, Cu—Zn—Zr—Al—O systems as well as $MgAl_2O_4$, $Ag/TiO_2$, $V_2O_5/TiO_2$, $Pt/TiO_2$, $Pt/Al_2O_3$, $Pt/CeZr$ oxides, $Pt/Cu/MnO_2$, $Pd/SiO_2$, $Pd/WO_3/ZrO_2$, $ZrO_2$, $ZnO_2/FeO/Al_2O_3$. Other examples include HSA alumina, Raney Cu on Pyrex, Cu flakes/chips, Cu over HSA silica and Cu over colloidal silica. Raney Ni can be used for hydrogenation pathways while Rh and Pt are also capable of facilitating the hydrolysis reactions. Further examples include supported or non-supported catalytic systems of the type ABCD-O, ABCD-P-O or ABCD, where A, B, C and D may represent any or a combination of Mo, V, Te, Ta, Si, Sb or Nb.

For example, the at least one carbohydrate can be a hexose, a pentose, or a mixture thereof.

For example, the at least one carbohydrate can be chosen from xylose, arabinose, lyxose, ribose, ribulose, xylulose, allose, altrose, glucose, mannose, gulose, idose, galactose, talose, and mixtures thereof.

For example, the at least one carbohydrate can be chosen from the family of aldopentoses, ketopentoses, aldohexoses, and/or ketohexoses, including their hemiacetals and hemiketals ring structures.

The at least one carbohydrate can be reacted with the metal catalyst at a temperature of about 240° C. to about 360° C., about 260° C. to about 320° C., about 275° C. to about 325° C., about 290° C. to about 310° C., or about 280° C. to about 300° C.

For example, the at least one organic acid can be chosen from acrylic acid, methacrylic acid, maleic acid, fumaric acid, acetic acid, and mixtures thereof.

For example, the methods can be carried out under conditions suitable for at least substantially preventing caramelization of the at least one carbohydrate. For example, the conditions suitable for at least substantially preventing caramelization of the at least one carbohydrate can comprise conditions at which caramelization of the at least one carbohydrate is slower than the reaction between the at least one carbohydrate and the at least one metal catalyst that produces the at least one organic acid or a derivative thereof. For example, the conditions suitable for at least substantially preventing caramelization of the at least one carbohydrate can comprise carrying out the reaction out at a temperature below a temperature at which caramelization of the at least one carbohydrate is faster than the reaction between the at least one carbohydrate and the at least one metal catalyst that produces the at least one organic acid or a derivative thereof.

Figure 2:
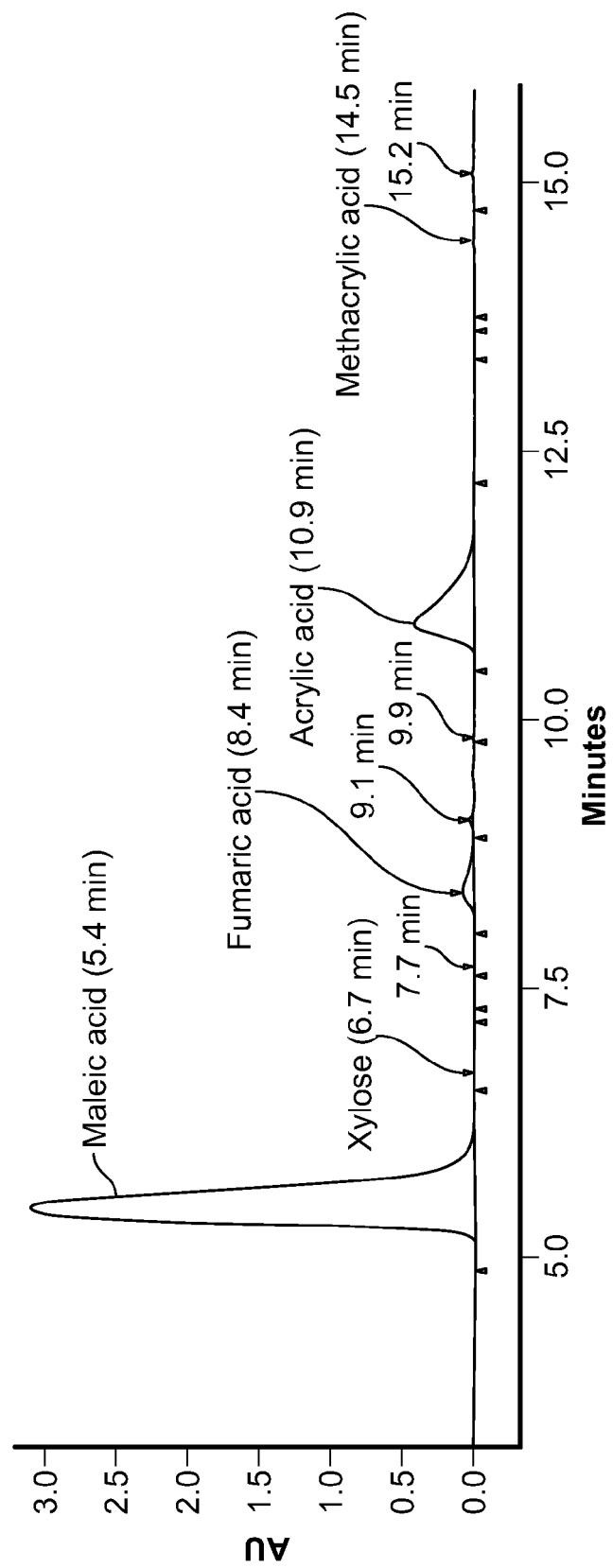
FIG. 2 represents High Pressure Liquid Chromatography (HPLC) results obtained from a sample prepared in accordance with an example of a method as described in the present disclosure.

Experiments of catalytic sugar oxidation process in a fluidized bed at high temperature have been carried out for the valorization of carbohydrates. Such experiments have been carried out using a fluidized bed as shown in FIG. 1. A aqueous solution of 10 wt % of xylose was injected to the fluidized catalyst bed at a rate of 0.5 mL/min via a metering pump. The fluidization gas was synthetic air (21% oxygen in argon) and the gas flow rate was 800-1000 ml/min and was controlled by a flow meter. About 200 g of a calcined VPO catalyst were used and the reaction temperature was about 300° C. and maintained by the heating elements (connected to thermocouple). The reactor temperature was stable throughout the reaction and no crystallization or deposition of sugar inside the bed was observed. In the conditions described above, about 24 g of solution were collected after 1 hour of reaction. It was analyzed by HPLC and GC (Gas Chromatography). The gas portion was analyzed by MS (Mass Spectrometry). FIG. 2, demonstrates a graphical view of the HPLC analysis results performed on the liquid produced from the reaction at 300° C. The HPLC analysis showed a range of organic acids and some other acid products. The major produced acids were maleic acid and acrylic acid. Moreover, methacrylic acid and fumaric acid were also observed.

The person skilled in the art would understand that, when applicable, all the various embodiments presented in the present disclosure can be used in combination with all the methods described in the "SUMMARY OF THE DISCLOSURE" section. Moreover, the person skilled in the art would understand that, when applicable, all the various embodiments presented in the present disclosure can be used in combination with any other embodiments presented in the present disclosure and/or in the "SUMMARY OF THE DISCLOSURE" section.

While a description was made with particular reference to the specific embodiments, it will be understood that numerous modifications thereto will appear to those skilled in the art. Accordingly, the above description and accompanying drawings should be taken as specific examples and not in a limiting sense.

What is claimed is:

1. A method for the valorization of carbohydrates, said method comprising:
reacting a fluid comprising at least one carbohydrate chosen from an hexose and a pentose, with at least one metal catalyst chosen from vanadium phosphorus oxide catalysts in a fluidized bed reactor so as to obtain at least one organic acid chosen from acrylic acid, methacrylic acid, maleic acid, fumaric acid and acetic acid.

2. The method of claim 1, wherein said method comprises injecting atomized droplets of a carbohydrate-containing composition that comprises said at least one carbohydrate and water into said fluidized bed reactor.

3. The method of claim 2, wherein said atomized droplets are vaporized in situ when inserted into said fluidized bed reactor.

4. The method of claim 1, wherein said fluid is synthetic air or air having a concentration of $O_2$ of about 0 to about 21%.

5. The method of claim 2, wherein said carbohydrate is at a concentration of about 1 wt % to about 20 wt %, based on the total weight of the carbohydrate-containing composition.

6. The method of claim 3, wherein said carbohydrate is at a concentration of about 8 wt % to about 12 wt %, based on the total weight of the carbohydrate-containing composition.

7. The method claim 2, wherein said composition is injected at a rate of about 0.5 mL/minute to about 10 mL/minute per about 0.2 L of capacity of said fluidized bed reactor.

8. The method of claim 5, wherein a fluidization gas is injected at a flow rate of about 400 mL/minute to about 2000 mL/minute per 0.2 L of capacity of said fluidized bed reactor.

9. The method of claim 1, wherein said at least one metal catalyst comprises $VOPO_4$, $VOHPO_4$, $(VO)_2P_2O_7$, $VO(PO_3)_2$, $VO(H_2PO_4)_2$ or mixtures thereof.

10. The method of claim 8, wherein said at least one metal catalyst comprises $VOPO_4$.

11. The method of claim 9, wherein said at least one carbohydrate is chosen from xylose, arabinose, lyxose, ribose, ribulose, xylulose, allose, altrose, glucose, mannose, gulose, idose, galactose, talose, and mixtures thereof.

12. The method of claim 10, wherein said at least one carbohydrate is reacted with said metal catalyst at a temperature of about 240° C. to about 360° C.

13. The method of claim 10, wherein said method is carried out under conditions suitable for at least substantially preventing caramelization of said at least one carbohydrate.

14. A method for the valorization of carbohydrates, said method comprising:
reacting a fluid comprising at least one carbohydrate chosen from an hexose and a pentose, with at least one metal catalyst chosen from vanadium phosphorus oxide catalysts under conditions suitable for at least substantially preventing caramelization of said at least one carbohydrate, so as to obtain at least one organic acid chosen from acrylic acid, methacrylic acid, maleic acid, fumaric acid and acetic acid.

15. A method for the valorization of carbohydrates, said method comprising:
reacting a fluid comprising at least one carbohydrate chosen from an hexose and a pentose, with at least one metal catalyst chosen from vanadium pyrophosphate, iron phosphate, $V_2O_5$, and mixtures thereof in a fluidized bed reactor so as to obtain at least one organic acid chosen from acrylic acid, methacrylic acid, maleic acid, fumaric acid and acetic acid.

* * * * *